(12) United States Patent
Yost et al.

(10) Patent No.: US 6,413,227 B1
(45) Date of Patent: Jul. 2, 2002

(54) METHOD AND APPARATUS FOR ASSESSMENT OF CHANGES IN INTRACRANIAL PRESSURE

(75) Inventors: William T. Yost, Newport News; John H. Cantrell, Williamsburg, both of VA (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 0 days.

(21) Appl. No.: 09/459,384

(22) Filed: Dec. 2, 1999

(51) Int. Cl.[7] .................................................. A61B 5/00
(52) U.S. Cl. ..................................... 600/561; 73/152.27
(58) Field of Search .............................. 600/587, 595, 600/437, 451, 561

(56) References Cited

U.S. PATENT DOCUMENTS

| | | | | |
|---|---|---|---|---|
| 3,554,186 A | * | 1/1971 | Leksell et al. ............... | 600/437 |
| 4,135,406 A | * | 1/1979 | Kretz ........................... | 73/620 |
| 4,624,142 A | | 11/1986 | Heyman | |
| 5,214,955 A | | 6/1993 | Yost et al. | |
| 5,379,770 A | * | 1/1995 | Van Veen ................... | 600/453 |
| 5,617,873 A | * | 4/1997 | Yost et al. ................... | 600/561 |
| 5,908,388 A | * | 6/1999 | Watkin et al. ............... | 600/438 |
| 6,117,089 A | * | 9/2000 | Sinha ........................... | 600/561 |

\* cited by examiner

*Primary Examiner*—Robert L. Nasser
*Assistant Examiner*—Pamela L Wingood
(74) *Attorney, Agent, or Firm*—Helen M. Galus (57) ABSTRACT

A non-invasive method and apparatus for monitoring changes in intracranial pressure which removes extracranial effects from the measurements. The method and apparatus can include the supplying of a fixed frequency electrical output to a transducer coupled to the patient's head, thereby generating an acoustical tone burst in the patient's head which generates a first echo and a second echo, the first echo reflecting from a first interface in the side of the patient's head coupled to the transducer, and the second echo reflecting from a second interface at the opposite side of the patient's head. The first and second echoes are received by the transducer which can generate a first electrical signal and a second electrical signal, wherein the first and second electrical signals vary in accordance with the corresponding first and second echoes. The counterbalancing phase shifts required to bring about quadrature between each of the first and second electrical signals and the fixed frequency electrical output can be measured, and values for the change in intracranial distance based on the changes in the counterbalancing phase shifts can be obtained.

42 Claims, 6 Drawing Sheets

METHOD AND APPARATUS FOR ASSESSMENT OF CHANGES IN INTRACRANIAL PRESSURE

ORIGIN OF INVENTION

The invention described herein was made by employees of the United States Government and may be manufactured and used by or for the Government for governmental purposes without payment of royalties thereon or therefor.

BACKGROUND OF THE INVENTION

1. Field of the Invention

This invention relates to measuring and monitoring of intracranial pressure changes in human patients, and more particularly to a non-invasive method and device for monitoring changes in intracranial pressure which removes extracranial effects from the measurements.

2. Background of the Invention

A prior method of measuring intracranial pressure included pulse phase-locked ultrasonic technology but this method did not include techniques nor refinements to remove extracranial effects from the measurements.

Another prior method includes an ultrasonic means to measure expansion of a pre-selected path through the cranial cavity by means of placement of a 500 KHz ultrasonic transducer at an appropriate location on the skull. In this technique, the measurement includes not only skull expansion, but also includes effects of edema and perfusion of tissues between the skin and the skull. This perfusion can result in measurements that are much larger than the path change due to cranial vault expansion alone.

Other measurement techniques such as strain sensor gauges located on a caliper can be placed across the cranial cavity for measurement. Such techniques, however, are also subject to the same problems associated with surface tissue edema and perfusion, similar to the ultrasonic technique.

Thus, although prior devices and methods are generally non-invasive, they are affected by surface tissue changes. These changes affect the accuracy of the determination of cranial vault expansion. In the above-mentioned techniques, the effects due to surface tissue could be eliminated, but that would require the excision of tissue around the connecting points (for the strain gauge caliper) or around the transducer point-of-contact (for the ultrasonic technique). This would make the techniques invasive, although not as invasive as drilling a hole through the cranium for insertion of a probe.

The present invention overcomes these and other disadvantages of the prior art by providing an improved method and device for measuring intracranial pressure changes and including the means to improve the accuracy of measurement of intracranial expansion.

BRIEF SUMMARY OF THE INVENTION

This invention is a method and device for measuring change in intracranial distances and includes calibration techniques necessary to convert these measurements to changes in intracranial pressure. It is an object of the invention to provide a non-invasive method and device for measuring change in intracranial distances which removes extracranial effects from the measurements, and to provide calibration techniques that enable that change in skull dimension to be related to the change in intracranial pressure. It is a further object to provide a non-invasive method for monitoring changes in intracranial pressure in human patients.

These and other objects of the invention are achieved by introducing known intracranial pressure changes using a non-invasive technique. The changes in skull dimension as a result of changes in intracranial pressure are then measured using a non-invasive device which removes extracranial effects (e.g., caused by changes in skin thickness and variation) from the measurement. The measured changes in skull dimension are then correlated to changes in intracranial pressure.

DETAILED DESCRIPTION OF INVENTION

An acoustic waveform will partially reflect from and partially transmit through an interface in a propagation medium if there exists a difference in the acoustic impedance (mass density times wave velocity) on either side of the interface. For example, in considering the propagation of a wave through a medium with two interfaces, each interface having a difference in acoustic impedance on either side of the interface, the reflection of the wave at the second interface is delayed with respect to the reflection at the first interface by the propagation time associated with the distance between the first and second interfaces and the sound velocity associated with the propagation medium between the two interfaces. This means that for pulse phase-locked loop systems (PPLLs) the reflected wave profile associated with the propagation time between the two interfaces will have no contribution from the propagation lying beyond the second interface.

Figure 2:
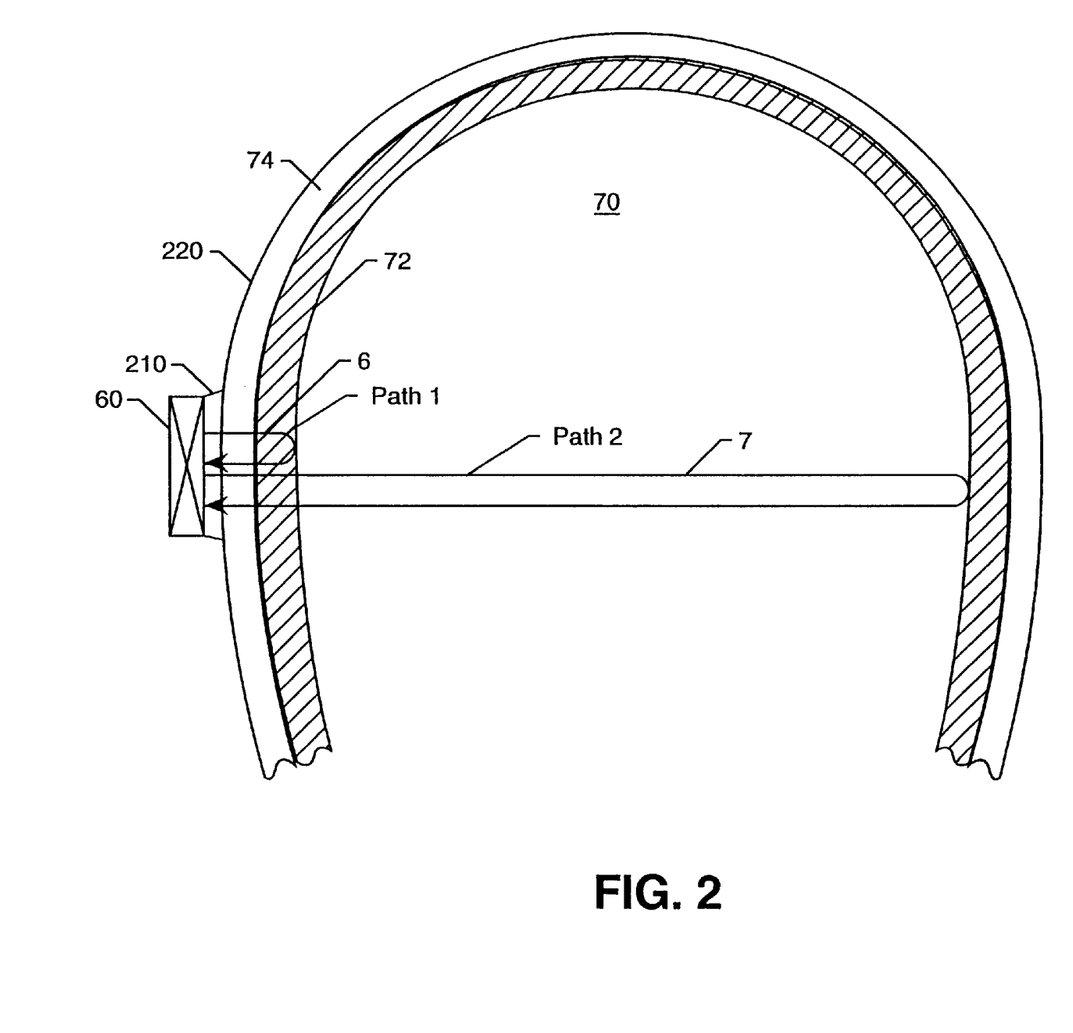
FIG. 2 is a cross-section of a front view of a transducer positioned against the skin of a patient.

With regard to the present invention, as illustrated in FIG. 2, this means that contributions to the acoustic waveform from the extracranial tissue 74 lying on the reflection side of the cranium from the transducer 60 may be eliminated by positioning the sample-and-hold 102, 108 of the PPLL only in a position corresponding to reflections from cranial bone 72.

Phase contributions to the PPLL phase-detector occur from various sources in the acoustic wave propagation path and from the PPLL instrument components. The principal wave propagation paths are those through extracranial tissue (skin 220, subcutaneous fat, blood vessels, etc.) 74, cranial bone 72, and intracranial tissue (brain tissue, ventricles, CSF, etc.) 70. The sound velocities of the various soft tissues are equal to within the overall measurement uncertainties of the present measurement configurations. Thus it is sufficiently accurate for present purposes to write the phase contributions from the extracranial tissue ($\phi_{ext}$) 74, the cranial bone ($\phi_{bn}$) 72, and intracranial tissue ($\phi_{int}$) 70 as:

$$\phi_{ext} = 2\pi f \frac{l_{ext}}{c_{ext}} \quad (1)$$

$$\phi_{bn} = 2\pi f \frac{l_{bn}}{c_{bn}} \quad (2)$$

$$\phi_{int} = 2\pi f \frac{l_{int}}{c_{int}} \quad (3)$$

where $f$ is the acoustic wave frequency, $1_{ext}$ is the path length and $c_{ext}$ is the sound velocity in extracranial tissue, $1_{bn}$ is the path length and $c_{bn}$ is the sound velocity in bone, and $1_{int}$ is the path length and $c_{int}$ is the sound velocity in intracranial tissue.

Consider now the total phase contribution resulting from an acoustic pulse traversing a single transcranial round trip (i.e., the first acoustic echo). Denoting a single round trip by a subscripted 1, we write the total phase $\phi_1$ as:

$$\phi_1 = 4\pi f \left[ \frac{l_{ext}}{c_{ext}} + \frac{l_{int}}{c_{int}} + \frac{l_{bn}}{c_{bn}} \right] + \gamma(f_1) \quad (4)$$

where the phase term $\gamma$ ($f_1$) is the phase contribution from the instrument electronic components.

For the variable frequency PPLL system (VFPPLL), quadruture conditions between the reference oscillator signal and the received acoustic signal are maintained such that any variation in $\phi_1$ is zero if $c_{ext} \cong c_{int}$ (i.e., assuming that the ultrasonic compressional velocity in brain tissue ($c_{int}$) is nearly equal to the ultrasonic compressional velocity in extracranial tissue ($c_{ext}$)), i.e., $$\Delta\phi_1 = \frac{4\pi f_1}{c}[\Delta l_{ext} + \Delta l_{int}] + \frac{4\pi \Delta f_1}{c}\left[l_{ext} + l_{int} + \frac{c}{c_{bn}}l_b\right] + \Delta\gamma(f_1) = 0 \quad (5)$$

where $\Delta\phi_1$ is the variation in $\phi_1$, $\Delta 1_{ext}$ is the variation in $1_{ext}$, $\Delta 1_{int}$ is the variation in $1_{int}$, and $\Delta\gamma(f_1)$ is the variation in $\gamma$ around $f_1$.

Similarly, the total phase contribution resulting from an acoustic pulse traversing two transcranial round trips (i.e., the second acoustic echo) is written as:

$$\phi_2 = 4\pi f_2 = \left[ \frac{l_{ext}}{c} + \frac{l_{bn}}{c_{bn}} + 2\frac{l_{int}}{c} \right] + \gamma(f_2) \quad (6)$$

where the subscripted 2 denotes second echo. We also have that:

$$\Delta\phi_2 = \frac{4\pi f_2}{c}[\Delta l_{ext} + 2\Delta l_{int}] + \frac{4\pi \Delta f_2}{c}\left[l_{ext} + 2l_{int} + \frac{c}{c_{bn}}l_{bn}\right] + \Delta\gamma(f_2) = 0 \quad (7)$$

in order to maintain quadrature conditions in the VFPPL system.

Solving equations (5) and (7) simultaneously for $\Delta 1_{int}$ we obtain:

$$\Delta l_{int} = l_{int}\left( \frac{\Delta f_1}{f_1} - 2\frac{\Delta f_2}{f_2} \right) + l_{int}\left( \frac{l_{ext}}{l_{int}} + \frac{c}{c_{bn}}\frac{l_{bt}}{l_{int}} \right)\left( \frac{\Delta f_1}{f_1} - \frac{\Delta f_2}{f_2} \right) + \frac{c}{4\pi}\left( \frac{d\gamma(f_1)}{df_1}\frac{\Delta f_1}{f_1} - \frac{d\gamma(f_2)}{df_2}\frac{\Delta f_2}{f_2} \right) \quad (8)$$

where we have set $$\Delta\gamma \frac{d\gamma(f_1)}{df_1}\Delta f_1, \text{ and } \Delta\gamma(f_2) = \frac{d\gamma(2_1)}{df_2}\Delta f_2.$$

In general, $$\frac{c}{c_{bn}}, \frac{l_{bn}}{l_{int}}, \text{ and } \frac{l_{ext}}{l_{int}}$$

are much smaller than unity. This means that the second term on the right-hand side of equation (8) is negligible compared to the first term on the right-hand side. The magnitude of the third term in the right-hand side of equation (8) is more difficult to estimate, since the functional dependence of $\gamma$ on frequency $f$ is generally not known a priori. Clearly, if the first and second echo signals are measured at the same frequency and frequency variations, then this term vanishes. Using typical commercially available damped transducers and low Q transducer material then $\gamma$ is small enough to be neglected. Otherwise, and for the general case, however, a procedure similar to that outlined in Appendix B of Yost, Cantrell, and Kuchnick (J. Acoust. Soc. Am. 91, 1456, 1992), which is incorporated herein by reference, must be followed to assess the magnitude of the third term on the right-hand side of equation (8).

For the constant frequency PPLL (CFPPLL) system, the problems associated with frequency variations disappear. For the CFPPLL, $f_1=f_2=f$=constant, $\gamma$=constant and $\Delta\phi_1 \neq 0$, $\Delta\phi_2 \neq 0$.

$$\Delta\phi_1 = \frac{4\pi f}{c}[l_{ext} + \Delta l_{int}] \quad (9)$$

$$\Delta\phi_2 = \frac{4\pi f}{c}[\Delta l_{ext} + 2\Delta l_{int}] \quad (10)$$

solving equations (9) and (10) for $\Delta 1_{int}$ we get:

$$\Delta l_{int} = \frac{c}{4\pi f}[\Delta\phi_2 - \Delta\phi_1] \quad (11)$$

Thus, direct measurements of the phase shifts $\Delta\phi 1$ and $\Delta\phi 2$ with the CFPPLL system allow a direct determination of $\Delta 1_{int}$.

Figure 1:
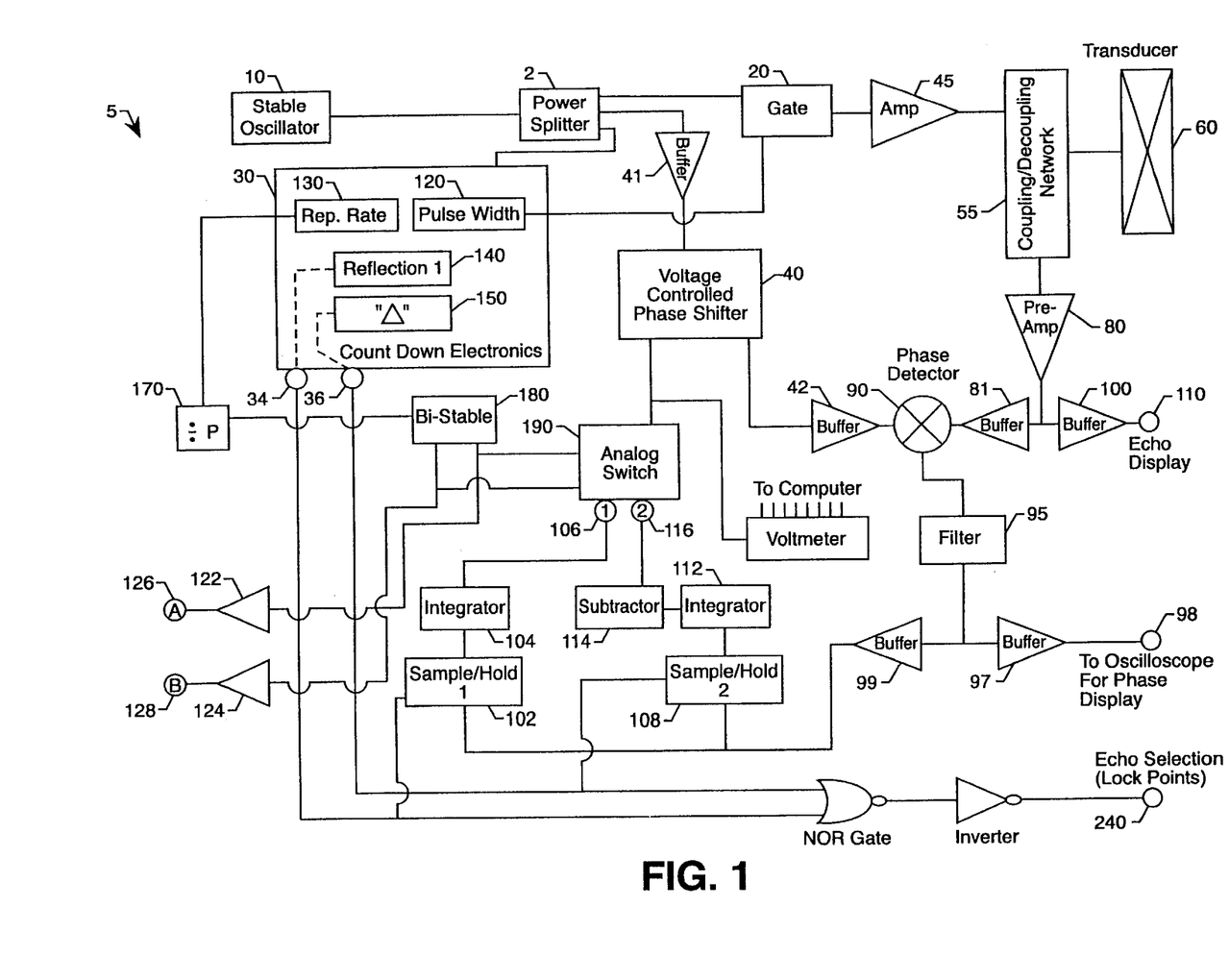
FIG. 1 illustrates a pulsed phase-locked circuit for measurement of intracranial pressure (phase control).

FIG. 1 shows the preferred embodiment of the present invention. Using the illustrated specialized circuit 5 for the measurement of intracranial expansion by bone-to-bone multiple reflection, the operation is as follows. A continuous wave generator 10 (labeled "stable oscillator") emits a continuous and stable voltage oscillation. This signal is sent through a power splitter 2 to the gate 20, the timing control, which, in this embodiment uses count down electronics 30, and through buffer 41 to the voltage-controlled phase shifter 40.

The tone burst, a measured segment of the continuous wave (typically 3–20 cycles) is formed, amplified 45 and sent through the coupling/decoupling network 55, and thus activates an ultrasonic mechanical oscillation of the transducer 60. Upon reception by the transducer of the ultrasonic signals and their consequent conversion into electrical signals, the coupling/decoupling network 55 routes the electrical signals to the preamplifier 80.

Figure 4:
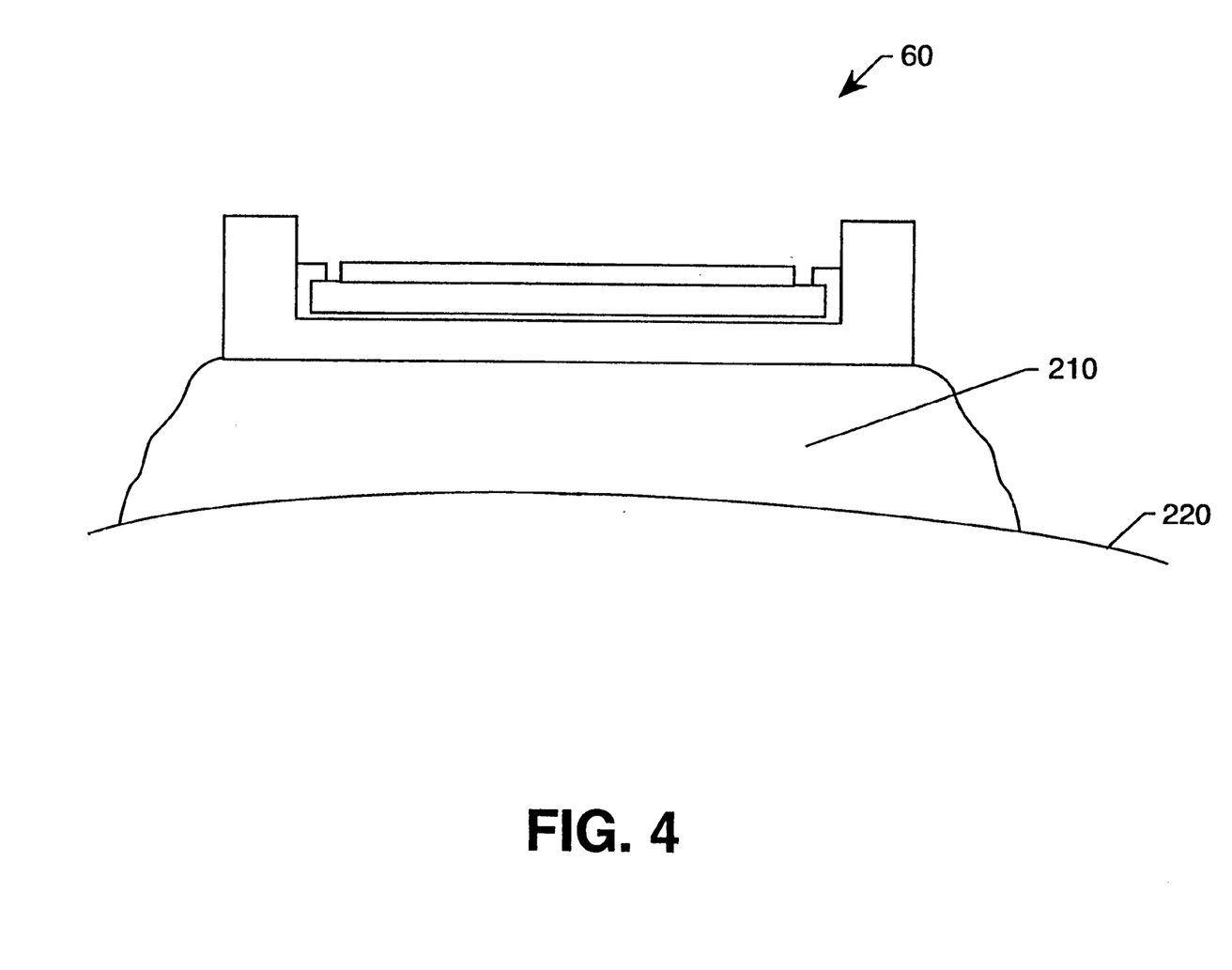
FIG. 4 is an expanded view of a transducer positioned against the skin of a patient.

As shown in FIG. 4, to prepare the transducer 60 for positioning on a patient, the transducer 60 is coated with a suitable amount of an appropriate ultrasonic conducting gel 210, cement, or similar material. The transducer 60 is then placed against the skin 220 on a patient's head, making certain that the gel 210 makes good contact between the skin 220 and the transducer. Although the above description applies to current ultrasonic measurement practices, it is understood that other methods of insertion and reception of acoustic or ultrasonic waves, including an air or other gas-filled gap, from patient's heads are permissible.

Figure 5:
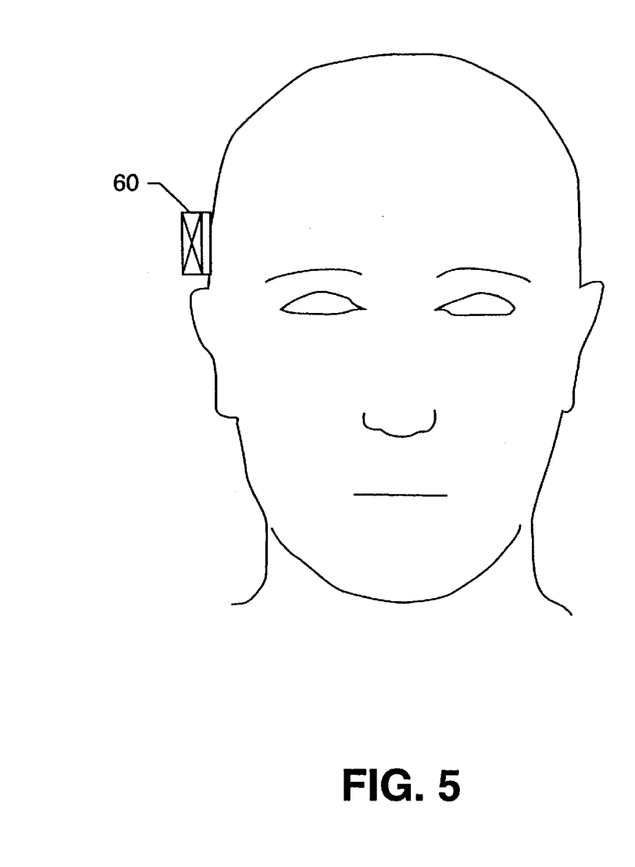
FIG. 5 is a front view of the head of a patient showing the transducer location.
Figure 6:
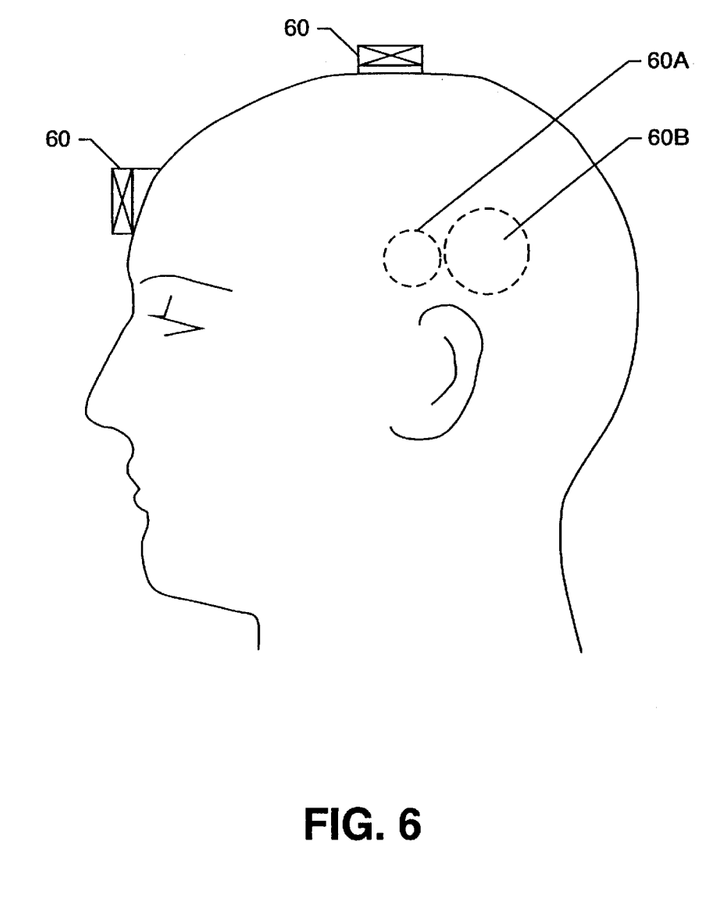
FIG. 6 is a side view of the head of a patient showing the range of transcranial location of the transducer.

FIGS. 5 and 6 show front and side views of a patient's head illustrating the location of the transducer 60 for transcranial mounting. The transducer 60 (shown in FIG. 5) may be mounted on either the left side or the right side of the head. FIG. 6 shows some of the possible locations 60A, 60B for the transducer 60. Although the operator preferably chooses the location to maximize the second echo, as indicated by the oscilloscope display 110, the only limitation on location of the transducer is the ability to obtain a second echo. Once this has been achieved, the transducer 60 may be held in place by any conventional method, including the use of an ace bandage, tape, or similar strap.

As illustrated in FIG. 2, the ultrasonic mechanical wave traverses along Path 1 6 through the extracranial tissue 74 and bone 72, and reflects off the proximate side of the patient's head at the interface of the bone 72 and the intracranial tissue 70, and traverses back through the bone 72 and the extracranial tissue 74 to be received by the transducer 60. Also, the ultrasonic mechanical wave traverses the extracranial tissue 74, cranial bone 72, and the intracranial tissue 70 in the cranial cavity along Path 2 7, reflects off the cranial bone 72 on the distal side of the patient's head, and traverses the bone 72 and extracranial tissue 74 of the proximate side of the patient's head to be received by the transducer 60. The transducer 60 converts the received ultrasonic waves traversing Paths 1 and 2 6, 7 into first and second electrical echo signals, respectively, which are routed by the coupling/decoupling network 55 through the preamp 80 and buffer 81 to the phase detector 90, which phase detector, in at least one embodiment, could be in the form of a mixer. The output of the preamp 80 is also made available through a buffer 100 for echo display 110 used in set up of the system.

The phase detector 90 phase-compares the received signal with the output of the stable oscillator 10 after passing through a voltage-controlled phase shifter 40 and forms voltage outputs which are proportional to the cosine of the phase difference between these two signals. Selection of the appropriate portion of the phase signal (i.e., reflection 1 or reflection 2) is accomplished by sample/hold 1 102 and sample/hold 2 108, respectively, under the control of the signals 34, 36 of the count down electronics 30. The integration of these voltages are obtained by typical integrator circuits, 112 or 104. These constitute the control voltages for the voltage controlled phase shifter 40. Phase output from the phase detector 90 is filtered by the filter 95 and is sent along two paths. The first path is buffered by a buffer 97 and then sent to an output 98. This output is displayed on an oscilloscope (not shown) for initial adjustments as described below. The second path goes through another buffer 99 to sample/hold 1 102. The output from sample/hold 1 102 then passes through an integrator 104 to the analog switch 190 as input 1 106. Similarly, the output from buffer 99 goes to sample/hold 2 108. The output from sample/hold 2 108 then passes through an integrator 112 and a phase subtractor 114 (i.e. phase inversion), and then to the analog switch 190 as input 2 116. The output of the analog switch 190 goes to the voltage controlled phase shifter 40 and to the voltmeter 160.

As the bi-stable circuit 180 changes states, the state change is made available for adjustment purposes through buffers 122 and 124, indicated on FIG. 1 by outputs A 126 and B 128. Outputs A 126 and B 128 designate received echo 1 or received echo 2, respectively. When output A 126 is high and output B 128 is low, the circuit 5 reads the phase shift of the first received echo. When output A 126 is low and output B 128 is high, the circuit 5 reads the phase shift of the second echo.

The count down electronics module 30 determines the pulse width 120 (the number of cycles in the tone burst); the repetition rate 130 (the number of tone bursts per second), Reflection 1 140, and Δ 150.

Reflection 1 140 generates the timing pulse 34 which selects a portion of the first echo. The phase comparison of this portion of the first echo is adjusted by a control voltage until quadrature is obtained. When quadrature is obtained, the control voltage is monitored by a voltmeter 160 connected to a data acquisition system (not shown) which includes a computer and appropriate software for data acquisition, processing, and display.

Similarly, Δ 150 generates the timing pulse 36 which selects a portion of the second echo. This adjustment permits location of the second reflection by entry of the number of oscillator cycles from the first reflection. The control voltage generated as for echo 1 controls the voltage control phase shifter 40. As with the Reflection 1 case, the voltage controlled phase shifter 40 is monitored by a voltmeter 160 connected to the computer. Δ 150 also determines the number of waves between a round-trip of the ultrasonic wave across the cranium 70.

Echo selection 240 aids in the appropriate alignment of the timing pulses to operate the sample/hold circuits 102, 108. When echo 1 is received, timing pulse 1 34 emanates from the count down electronics 30 which causes sample/ hold 1 102 to sample and hold the phase comparison of echo 1 with the oscillator 10. Likewise, timing pulse 2 36 from the count down electronics 30 causes sample/hold 2 108 to sample and hold the phase comparison of echo 2 with the oscillator 10.

The appropriate phase shifts of echo 1 and echo 2 are measured alternately with the ÷P circuit 170, the bi-stable circuit 180 and the analog switch 190. P is an integer that can be set and represents the number of repetitions used to give a stable measurement of the control voltage for quadrature of echo 1 with stable oscillator 10. Then the circuit causes the measurement of the control voltage for quadrature of echo 2 with stable oscillator 10 to be stabilized and recorded. The process alternates as long as measurements are made.

The computer alternately records two sets of data. The first set is the control voltage associated with echo 1. The second set is the control voltage associated with echo 2. Each control voltage is related to its corresponding phase shift by the transfer function of the voltage controlled phase shifter 40. These phase shifts can be used to calculate the path expansion, in its most general form, by the equation:

$$\Delta x = x \frac{\Delta \phi}{\phi} \tag{12}$$

where Δx is the path expansion, x the path length is equal to Path 2−Path 1, Δø is the total phase shift (i.e., sum of the phase shifts), and ø is the initial phase of the wave across the cranium 70. In the case where the velocity of compressional wave propagation in human brain tissue does not appreciably change with intracranial pressure, the above equation can be written as:

$$\Delta x = \frac{C(T)}{\omega \Delta \phi} \quad (13)$$

where C(T) is the velocity of compressional wave propagation in human brain tissue as a function of temperature, and ω=2πf, where f is the frequency in Hz. We assume that during the measurement period, temperature is stable.

By analysis of the ultrasonic waves we can write the path expansion by:

$$\Delta x = x \left[ \frac{\Delta \phi}{\phi_{Echo_2}} - \frac{\Delta \phi}{\phi_{Echo_1}} \right] \quad (14)$$

Figure 3:
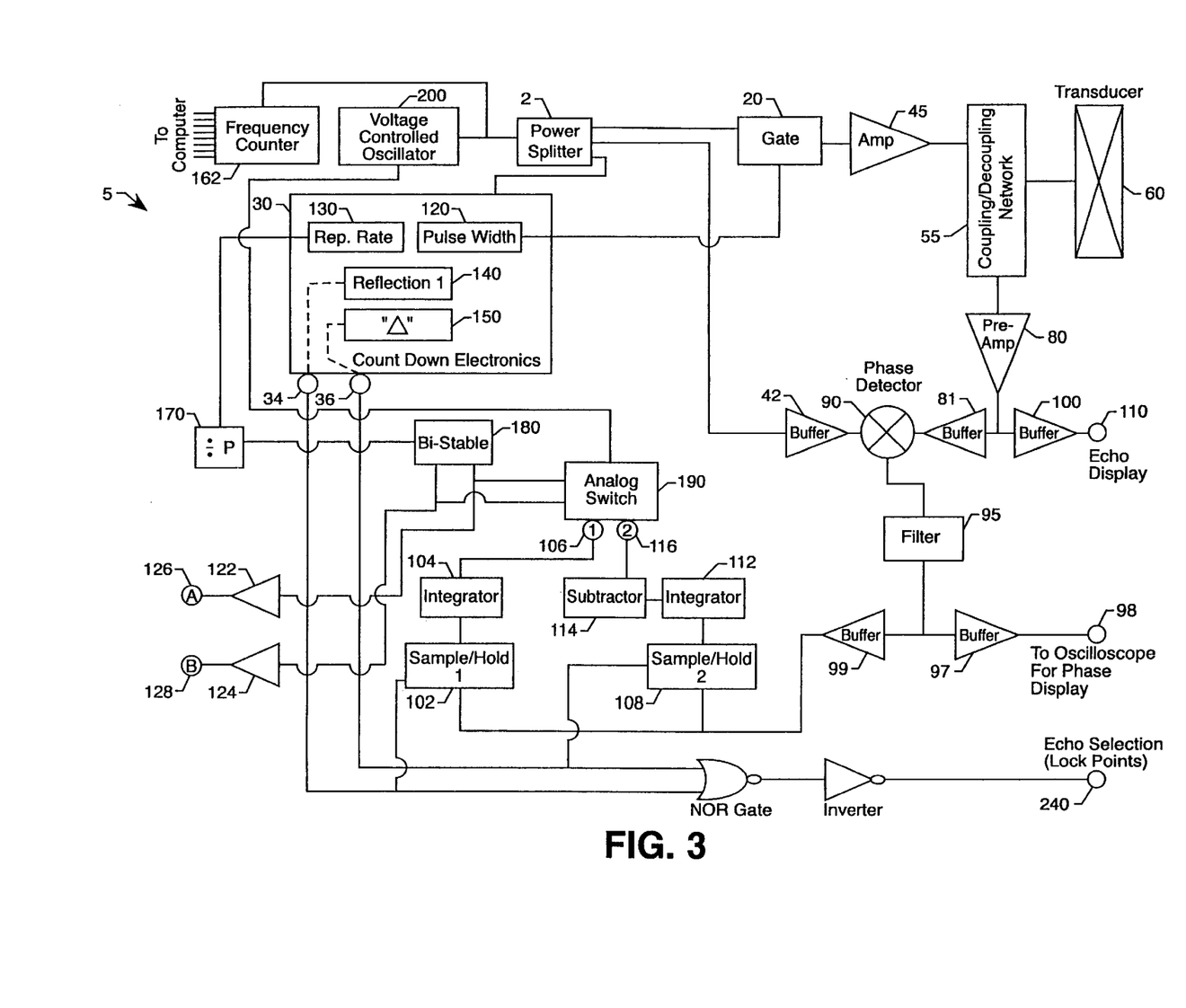
FIG. 3 illustrates a pulsed phase-locked circuit for measurement of intracranial pressure (frequency control) using multiple reflections.

A second embodiment of the present invention is shown in FIG. 3. This embodiment works similarly to the first, except that a voltage controlled oscillator 200 generates oscillator frequency changes to bring about quadrature for each echo. As in the preferred embodiment, the ÷P circuit 170, the bi-stable circuit 180 and the analog switch 190 work together to alternately select which signal (106 or 116) controls quadrature, in this case by controlling frequency. For this second embodiment, there is an inherent instrument error, due to electronics sensitivity to frequency changes. This error is typically no more than 15%. The equation for calculation of path expansion is, for the second embodiment:

$$\Delta x = x \left[ \frac{\Delta f}{f_{Echo_1}} - \frac{\Delta f}{f_{Echo_2}} \right] \quad (15)$$

where f and Δf are measured by the frequency counter 162.

Figure 7:
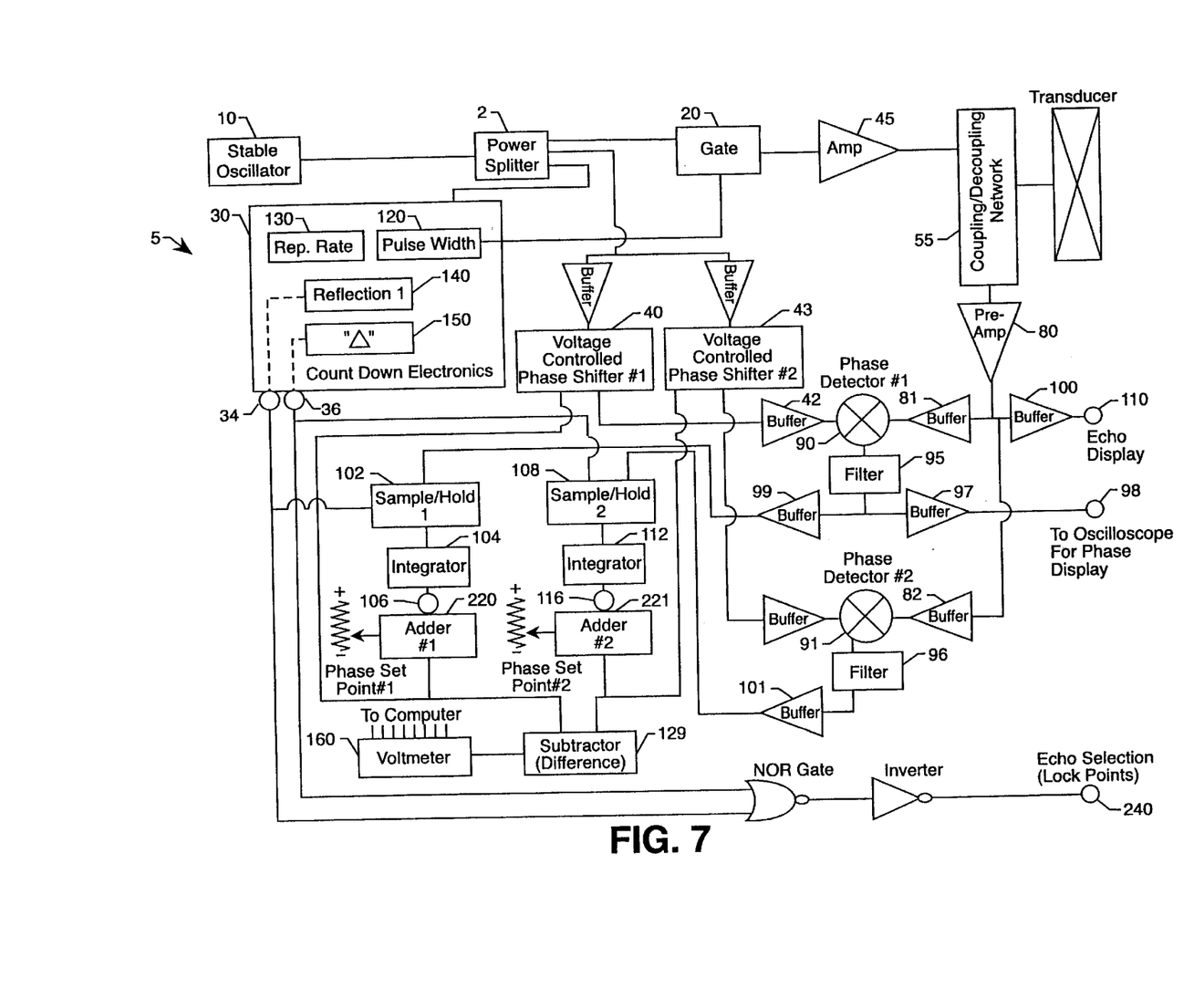
FIG. 7 is another embodiment of a pulsed phase-locked circuit for measurement of intracranial pressure according to the present invention.

A third embodiment of the present invention, as shown in FIG. 7, offers the advantages of near simultaneous measurement of both echoes, avoidance of switching transients, shorter response time, and requires a smaller dose of ultrasonic power. This embodiment is similar to the embodiment of FIG. 1, except for: sample and hold 1 102 captures the phase comparison of the echo 1 signal with the stable oscillator signal fed through the voltage controlled phase shifter 1 40 and holds its value. Sample and hold 2 108 captures the phase comparison of the echo 2 signal with the stable oscillator signal fed through voltage controlled phase shifter 2 43 and holds its value. These signals are then fed to their respective integrators 104, 112 so that:

a) a phase shifter control voltage is developed by integrator 1 104 that will produce quadrature with echo 1 signal, while, nearly simultaneously;

b) a phase shifter control voltage is developed by integrator 2 112 that will give quadrature with echo 2 signal; and c) the control voltage applied to voltage controlled phase shift 1 40 is subtracted from the control voltage applied to voltage controlled phase shift network 2 43 by the difference circuit 129; this voltage then "follows" the path expansion (Δx). It is understood that the true change in intracranial distance is one-half of the path expansion. Adder 211 and adder 221 were incorporated to improve response time.

In constant frequency systems as shown in FIGS. 7 and 1, all of the functions can be performed with digital electronics. As an example, rather than detecting the phase differences between the echo signals and reference signal, and using the integrated phase difference to drive the signals to quadrature, the echo signals and the reference signal can be digitally recorded, and the phase difference determined by use of computer algorithms. As further example, timing control, gating, waveform generation (synthesizer), coupling/decoupling function, and even the preamp function, can be performed by digital electronics or an appropriately programmed digital computer.

Various methods may be used to establish a relationship between changes in intracranial distance with known changes in transcranial pressure (pressure gauge), as for example disclosed in U.S. Pat. No. 5,617,873 issued to Yost et al. at column 5, line 32 thru column 6, line 14, which is incorporated herein by reference.

It should be understood by those skilled in the art that the descriptions and illustrations herein are by way of examples and the invention is not limited to the exact details shown and described. For example, although the embodiment shown in FIG. 1 includes a voltage controlled phase shifter, it should be understood that any device that produces a controlled phase shift in response to a control signal may be used; for example, a current controlled phase shifter or an optically controlled phase shifter. And, although the invention is illustrated using a mixer, any means of phase detection may be used; for example, a synchronous detector, a homodyne detector, an analog mixer, or a digital mixer.

What is claimed is:

1. An apparatus for measuring phase shift in the head of a patient, the patient's head having layers comprised of skin, subcutaneous tissue, bone and intracranial tissue, wherein the interface between the bone and the intracranial tissue is a first interface and the interface between the intracranial tissue and the bone on the opposite side of the patient's head is a second interface, the apparatus comprising:

a logic and timing circuit;

a variable phase shift circuit;

a tone burst formation gate;

a fixed frequency oscillator coupled to and sending a constant frequency output to the logic and timing circuit, the variable phase shift circuit as a reference signal, and the tone burst formation gate;

a transducer coupled to the tone burst formation gate and being acoustically coupled to the skin of the patient's head, so that an electrical tone burst is sent to the transducer which generates a first echo and a second echo in the patient's head, the first echo reflecting from the first interface in the side of the patient's head coupled to the transducer and the second echo reflecting from the second interface at the other side of the patient's head, the first and second echos being received by the transducer which generates a first electrical echo signal and a second electrical echo signal, wherein the first and second electrical echo signals vary in accordance with the corresponding first and second echos;

means for receiving and comparing phases of the first and second electrical signals and the reference signal, and outputting error signal voltages when the phases of the first and second electrical signals and the reference signal are not in quadrature;

a first sample and hold circuit and a second sample and hold circuit, wherein the first and second sample and hold circuits receive a corresponding one of the error signal voltages and pass the error signal voltages to integrator circuits which provide control signals for the variable phase shift circuit;

means for measuring control signals from the integrator circuits which bring about quadrature via the variable phase shift circuit with the reference signal; and means for combining the control signals of the integrator circuits that control the variable phase shift circuit to bring about the quadrature with each electrical echo signal to remove extracranial effects from the measurements.

2. The apparatus of claim 1, wherein the means for measuring the control signals from the integrator circuits comprises a voltmeter.

3. The apparatus of claim 1, wherein the means for combining the control signals from the integrator circuits comprises a data acquisition system.

4. The apparatus of claim 2, wherein the means for combining the control signals from the integrator circuits comprises a data acquisition system.

5. A non-invasive method of measuring phase shift in the head of a patient, the patient's head having layers comprised of skin, subcutaneous tissue, bone and intracranial tissue, wherein the interface between the bone and the intracranial tissue is a first interface and the interface between the intracranial tissue and the bone on the opposite side of the patient's head from the first interface is a second interface, the method comprising the steps of:

(a) supplying a fixed frequency electrical output to a transducer coupled to the patient's head, thereby generating an acoustical tone burst in the patient's head which generates a first echo and a second echo, the first echo reflecting from the first interface in the side of the patient's head coupled to the transducer and the second echo reflecting from the second interface at the opposite side of the patient's head, the first and second echoes being received by the transducer which generates a first electrical signal and a second electrical signal, wherein the first and second electrical signals vary in accordance with the corresponding first and second echoes; and (b) measuring counterbalancing phase shifts required to bring about quadrature between each of the first and second electrical signals and the fixed frequency electrical output.

6. The method of claim 5, wherein the measuring includes:

comparing the phase of the fixed frequency electrical output and the first and second electrical echo signals to provide error voltage signals in accordance with the phase differences between the fixed frequency electrical output and the first and second electrical echo signals;

outputting the error signal voltages through a corresponding first sample and hold circuit and a second sample and hold circuit and then through corresponding integrator circuits which provide control signals to a variable phase shift circuit;

measuring the output of the integrator circuits; and controlling the variable shift circuit with the outputs of the integrator circuits to bring about quadrature of the fixed frequency electrical output with each electrical echo signal.

7. A non-invasive method of measuring change in intracranial distance in the head of a patient, the patient's head having layers comprised of skin, subcutaneous tissue, bone and intracranial tissue, wherein the interface between the bone and the intracranial tissue is a first interface and the interface between the intracranial tissue and the bone on the opposite side of the patient's head is a second interface, the method comprising the steps of:

(a) supplying a fixed frequency electrical output to a transducer coupled to the patient's head, thereby generating an acoustical tone burst in the patient's head which generates a first echo and a second echo, the first echo reflecting from the first interface in the side of the patient's head coupled to the transducer and the second echo reflecting from the second interface at the other side of the patient's head, the first and second echoes being received by the transducer which generates a first electrical signal and a second electrical signal, wherein the first and second electrical signals vary in accordance with the corresponding first and second echoes;

(b) measuring counterbalancing phase shifts required to bring about quadrature between the first and second electrical signals and the fixed frequency electrical output; and (c) obtaining values for the change in intracranial distance based on the changes in the counterbalancing phase shifts.

8. The method of claim 7, wherein the measuring includes:

comparing the phase of the fixed frequency electrical output and the first and second electrical echo signals to provide error voltage signals in accordance with the phase differences between the fixed frequency electrical output and the first and second electrical echo signals;

outputting the error signal voltages through a corresponding first sample and hold circuit and a second sample and hold circuit and then through corresponding integrator circuits which provide control signals for a variable phase shift circuit;

measuring the output of the integrator circuits; and controlling the variable phase shift circuit with outputs of the integrator circuits to bring about quadrature of the fixed frequency electrical output with each electrical echo signal.

9. A non-invasive method for measurement of change in intracranial pressure in a patient, comprising the steps of:

(a) calibrating a measuring device by introducing known changes in intracranial pressure and reading the corresponding phase correction differences between two echoes, one echo each from the cranial structure on opposing sides of the head of the patient, to permit the removal of the effects of extracranial tissue; and (b) obtaining values for change in intracranial pressure for the patient based on the values for change in the phase correction differences.

10. The non-invasive method for measurement of change in intracranial pressure in a patient according to claim 9, wherein the measuring device comprises an ultrasonic pulsed echo system.

11. The method of 10, wherein the calibrating step includes means for inducing known changes in intracranial pressure.

12. The method of 11, wherein the means for inducing known changes in intracranial pressure comprises a tilt bed.

13. The method of 11, wherein the means for inducing known changes in intracranial pressure comprises a counter-pressure helmet.

14. An apparatus for measuring phase shift in the head of a patient, the patient's head having layers comprised of skin, subcutaneous tissue, bone and intracranial tissue, wherein the interface between the bone and the intracranial tissue is a first interface and the interface between the intracranial tissue and the bone on the opposite side of the patient's head is a second interface, the apparatus comprising:

a logic and timing circuit;

a tone burst formation gate;

a voltage controlled oscillator coupled to and sending a variable frequency output to the logic and timing circuit, and the tone burst formation gate;

a transducer coupled to the tone burst formation gate and being acoustically coupled to the skin of the patient's head, so that an electrical tone burst is sent to the transducer which generates a first echo and a second echo in the patient's head, the first echo reflecting from the first interface in the side of the patient's head coupled to the transducer and the second echo reflecting from the second interface at the other side of the patient's head, the first and second echos being received by the transducer which generates a first electrical echo signal and a second electrical echo signal, wherein the first and second electrical echo signals vary in accordance with the corresponding first and second echos;

means for receiving and comparing phases of the first and second electrical signals and the signal from the voltage controlled oscillator, and outputting error signal voltages when the phases of the first and second electrical signals and the voltage controlled oscillator signal are not in quadrature;

a first sample and hold circuit and a second sample and hold circuit, wherein the first and second sample and hold circuits receive a corresponding one of the error signal voltages and pass the error signal voltages to integrator circuits which provide control signals for the voltage controlled oscillator;

means for measuring the frequency of the voltage controlled oscillator signal; and means for combining the control signals of the integrator circuits that control the voltage controlled oscillator to bring about quadrature of the voltage controlled oscillator signal with each electrical echo signal to remove extracranial effects from the measurements.

15. The apparatus of claim 12, wherein the means for measuring the frequency of the voltage controlled oscillator signal comprises a frequency counter.

16. The apparatus of claim 12, further comprising:

means for combining the frequency measurements; and said means for combining the frequency measurements comprises a data acquisition system.

17. The apparatus of claim 15, further comprising:

means for combining the frequency measurements; and the means for combining the frequency measurements comprises a data acquisition system.

18. A non-invasive method of measuring phase shift in the head of a patient, the patient's head having layers comprised of skin, subcutaneous tissue, bone and intracranial tissue, wherein the interface between the bone and the intracranial tissue is a first interface and the interface between the intracranial tissue and the bone on the opposite side of the patient's head from the first interface is a second interface, the method comprising the steps of:

(a) supplying a controlled frequency electrical output to a transducer coupled to the patient's head, thereby generating an acoustical tone burst in the patient's head which generates a first echo and a second echo, the first echo reflecting from the first interface in the side of the patient's head coupled to the transducer and the second echo reflecting from the second interface at the opposite side of the patient's head, the first and second echoes being received by the transducer which generates a first electrical signal and a second electrical signal, wherein the first and second electrical signals vary in accordance with the corresponding first and second echoes; and (b) measuring counterbalancing frequency shifts required to bring about quadrature between each of the first and second electrical signals and the controlled frequency electrical output.

19. The method of claim 18, wherein the measuring includes:

comparing the phase of the controlled frequency electrical output and the first and second electrical echo signals to provide error voltage signals in accordance with the phase differences between the controlled frequency electrical output and the first and second electrical echo signals;

outputting the error signal voltages through a corresponding first sample and hold circuit and a second sample and hold circuit and then through corresponding integrator circuits which provide control signals to the source of the controlled frequency electrical output; and controlling the source of the controlled frequency electrical output with outputs of the integrator circuits to bring about quadrature of the controlled frequency electrical output with each electrical echo signal.

20. A non-invasive method of measuring change in intracranial distance in the head of a patient, the patient's head having layers comprised of skin, subcutaneous tissue, bone and intracranial tissue, wherein the interface between the bone and the intracranial tissue is a first interface and the interface between the intracranial tissue and the bone on the opposite side of the patient's head is a second interface, the method comprising the steps of:

(a) supplying an electrical output to a transducer coupled to the patient's head, thereby generating an acoustical tone burst in the patient's head which generates a first echo and a second echo, the first echo reflecting from the first interface in the side of the patient's head coupled to the transducer and the second echo reflecting from the second interface at the other side of the patient's head, the first and second echoes being received by the transducer which generates a first electrical signal and a second electrical signal, wherein the first and second electrical signals vary in accordance with the corresponding first and second echoes;

(b) measuring counterbalancing frequency shifts required to bring about quadrature between the first and second electrical signals and the electrical output; and (c) obtaining values for the change in intracranial distance based on the changes in the counterbalancing frequency shifts.

21. The method of claim 20, wherein the measuring includes:

comparing the phase of the electrical output and the first and second electrical echo signals to provide error voltage signals in accordance with the phase differences between the electrical output and the first and second electrical echo signals;

outputting the error signal voltages through a corresponding first sample and hold circuit and a second sample and hold circuit and then through corresponding integrator circuits which provide control signals for the source of the electrical output;

measuring the frequency of the electrical output; and controlling the source of the electrical output with outputs of the integrator circuits to bring about quadrature of the electrical output with each electrical echo signal.

22. An apparatus for measuring phase shift in the head of a patient, the patient's head having layers comprised of skin, subcutaneous tissue, bone and intracranial tissue, wherein the interface between the bone and the intracranial tissue is a first interface and the interface between the intracranial tissue and the bone on the opposite side of the patient's head is a second interface, the apparatus comprising:

a logic and timing circuit;

two voltage controlled phase shift circuits;

a tone burst formation gate;

a fixed frequency oscillator coupled to and sending a constant frequency output to the logic and timing circuit as a clock signal, the two voltage controlled phase shift circuits as reference signals, and the tone burst formation gate;

a transducer coupled to the tone burst formation gate and being acoustically coupled to the skin of the patient's head, so that an electrical tone burst is sent to the transducer which generates a first echo and a second echo in the patient's head, the first echo reflecting from the first interface in the side of the patient's head coupled to the transducer and the second echo reflecting from the second interface at the other side of the patient's head, the first and second echos being received by the transducer which generates a first electrical echo signal and a second electrical echo signal, wherein the first and second electrical echo signals vary in accordance with the corresponding first and second echos;

means for receiving and comparing phases of the first and second electrical signals and their corresponding reference signals, and outputting error signal voltages when the phases of the first and second electrical signals and their corresponding reference signals are not in quadrature;

a first sample and hold circuit and a second sample and hold circuit, wherein the first and second sample and hold circuits receive a corresponding one of the error signal voltages and pass the error signal voltages to integrator circuits which provide control signals for a corresponding one of the voltage controlled phase shift circuits; and means for combining the control signals of the integrator circuits that control the voltage controlled phase shift circuits to bring about quadrature of each of the electrical echo signals with its corresponding reference signal to remove extracranial effects from the measurements.

23. The apparatus of claim 22, further comprising means for measuring the output from the means for combining the control signals of the integrator circuits.

24. The apparatus of claim 22, further comprising a data acquisition system operatively connected to the output measuring means.

25. The apparatus of claim 23, further comprising a data acquisition system operatively connected to the output measuring means.

26. The apparatus of claim 25, further comprising means for adding an adjustable offset to the control signals of the integrator circuits.

27. A non-invasive method of measuring phase shift in the head of a patient, the patient's head having layers comprised of skin, subcutaneous tissue, bone and intracranial tissue, wherein the interface between the bone and the intracranial tissue is a first interface and the interface between the intracranial tissue and the bone on the opposite side of the patient's head from the first interface is a second interface, the method comprising the steps of:

(a) supplying a fixed frequency electrical output to a transducer coupled to the patient's head, thereby generating an acoustical tone burst in the patient's head which generates a first echo and a second echo, the first echo reflecting from the first interface in the side of the patient's head coupled to the transducer and the second echo reflecting from the second interface at the opposite side of the patient's head, the first and second echoes being received by the transducer which generates a first electrical signal and a second electrical signal, wherein the first and second electrical signals vary in accordance with the corresponding first and second echoes; and (b) measuring substantially simultaneously counterbalancing phase shifts required to bring about quadrature between each of the first and second electrical signals and the fixed frequency electrical output.

28. The method of claim 27, wherein the measuring includes:

comparing the phase of the fixed frequency electrical output and the first and second electrical echo signals to provide error voltage signals in accordance with the differences between the fixed frequency electrical output and the first and second electrical echo signals;

outputting the error signal voltages through a corresponding first sample and hold circuit and a second sample and hold circuit and then through corresponding integrator circuits which each provide a control signal to a corresponding variable phase shift circuit; and controlling the corresponding variable phase shift circuits with outputs of the integrator circuits to bring about quadrature of the fixed frequency electrical output with each electrical echo signal.

29. The method of claim 28, wherein the measuring further comprises determining the difference between the two corresponding control signals utilizing a subtractor and voltmeter.

30. A non-invasive method of measuring change in intracranial distance in the head of a patient, the patient's head having layers comprised of skin, subcutaneous tissue, bone and intracranial tissue, wherein the interface between the bone and the intracranial tissue is a first interface and the interface between the intracranial tissue and the bone on the opposite side of the patient's head is a second interface, the method comprising the steps of:

(a) supplying a fixed frequency electrical output to a transducer coupled to the patient's head, thereby generating an acoustical tone burst in the patient's head which generates a first echo and a second echo, the first echo reflecting from the first interface in the side of the patient's head coupled to the transducer and the second echo reflecting from the second interface at the other side of the patient's head, the first and second echoes being received by the transducer which generates a first electrical signal and a second electrical signal, wherein the first and second electrical signals vary in accordance with the corresponding first and second echoes;

(b) measuring substantially simultaneously counterbalancing phase shifts required to bring about quadrature between the first and second electrical signals and the fixed frequency electrical output; and (c) obtaining values for the change in intracranial distance based on the changes in the counterbalancing phase shifts.

31. The method of claim 30, wherein the measuring includes:

comparing the phase of the fixed frequency electrical output and the first and second electrical echo signals to provide error voltage signals in accordance with the differences between the fixed frequency electrical output and the first and second electrical echo signals;

outputting the error signal voltages through a corresponding first sample and hold circuit and a second sample and hold circuit and then through corresponding integrator circuits which provide control signals for corresponding variable phase shift circuits; and controlling the corresponding variable phase shift circuits with outputs of the integrator circuits to bring about quadrature of the fixed frequency electrical output with each electrical echo signal.

32. The method of claim 31, wherein the measuring further comprises determining the difference between the two corresponding control signals utilizing a subtractor and voltmeter.

33. An apparatus for measuring phase shift in the head of a patient, the patient's head having layers comprised of skin, subcutaneous tissue, bone and intracranial tissue, wherein the interface between the bone and the intracranial tissue is a first interface and the interface between the intracranial tissue and the bone on the opposite side of the patient's head is a second interface, the apparatus comprising:

means for producing and transmitting an electrical tone burst from a reference signal;

means for receiving the electrical tone burst and in response generating a first and second echo in the head of a patient, the first echo reflecting from the first interface in the patient's head and the second echo reflecting from the second interface in the patient's head;

means for receiving the reflected first and second echoes and generating corresponding first and second electrical echo signals;

means for receiving and comparing the phases of the first and second electrical echo signals with a reference signal; and means for adjusting the phases of the first and second electrical signal in relation to the reference signal to remove extracranial effects from the measurements and thereby permit the determination of the phase shift in the head of a patient.

34. The apparatus for measuring phase shift in the head of a patient according to claim 33, wherein the measured phase shift corresponds to the difference between the phase adjustments to the first and second electrical signals, thereby removing the extracranial effects from the measurements.

35. The apparatus for measuring phase shift in the head of a patient according to claim 34, further comprising:

means for comparing two or more measured phase shifts in the head of a patient to determine changes in intracranial pressure.

36. An apparatus for measuring change in intracranial distance in the head of a patient, the patient's head having layers comprised of skin, subcutaneous tissue, bone and intracranial tissue, wherein the interface between the bone and the intracranial tissue is a first interface and the interface between the intracranial tissue and the bone on the opposite side of the patient's head is a second interface, the apparatus comprising:

means for producing a fixed frequency electrical output;

means for receiving the electrical output and in response generating an acoustical tone burst in the patient's head which generates a first and second echo in the head of a patient, the first echo reflecting from the first interface in the patient's head and the second echo reflecting from the second interface in the patient's head;

means for receiving the reflected first and second echoes and generating corresponding first and second electrical echo signals;

means for measuring counterbalancing phase shifts required to bring about a desired phase shift between each of the first and second electrical signals and the fixed frequency electrical output, wherein the difference between the phase adjustments to the first and second electrical signals corresponds to the phase shift in the head of the patient; and means for comparing two or more measured phase shifts in the head of a patient to determine changes in intracranial distance.

37. An apparatus for measuring change in intracranial distance in the head of a patient, the patient's head having layers comprised of skin, subcutaneous tissue, bone and intracranial tissue, wherein the interface between the bone and the intracranial tissue is a first interface and the interface between the intracranial tissue and the bone on the opposite side of the patient's head is a second interface, the apparatus comprising:

means for producing a variable frequency electrical output;

means for receiving the electrical output and in response generating a tone burst in the patient's head which generates a first and second echo in the head of a patient, the first echo reflecting from the first interface in the patient's head and the second echo reflecting from the second interface in the patient's head;

means for receiving the reflected first and second echoes and generating corresponding first and second electrical echo signals; and means for measuring counterbalancing shifted frequencies required to bring about a predetermined phase shift between each of the first and second electrical signals and the frequency electrical output, wherein the change in the intracranial distance corresponds to changes in the differences between the two frequencies for the first and second echoes.

38. An apparatus for measuring a change in intercranial pressure in the head of a patient, the patient's head having layers comprised of skin, subcutaneous tissue, bone and intracranial tissue, wherein the interface between the bone and the intracranial tissue is a first interface and the interface between the intracranial tissue and the bone on the opposite side of the patient's head is a second interface, the apparatus comprising:

means for producing and transmitting an electrical tone burst;

means for receiving the electrical tone burst and in response generating a first and second echo in the head of a patient, the first echo reflecting from the first interface in the patient's head and the second echo reflecting from the second interface in the patient's head;

means for receiving the reflected first and second echoes and generating corresponding first and second electrical echo signals;

means for receiving and comparing the first and second electrical echo signals with a reference signal;

means for shifting the phases of the first and second electrical echo signals in relation to the reference signal to remove extracranial effects from the measurements; and means for measuring the phase shifts and utilizing these measurements to calculate a change in intracranial pressure in the patient's head.

39. The apparatus for measuring a change in intracranial pressure according to claim 38, wherein the means for measuring the phase shifts and utilizing these measurements to calculate a change in intracranial pressure comprises means for determining the changes in the differences between the measured phase shifts for the first and second electrical echo signals.

40. A non-invasive method for measurement of change in intracranial pressure in a patient, comprising the steps of:

(a) calibrating a measurement device by introducing known changes in intracranial pressure and reading the corresponding phase differences between two echoes produced by the cranial structure, to permit the removal of the effects of extracranial tissue; and (b) obtaining values for change in intracranial pressure for the patient based on the values for change in the phase differences.

41. The non-invasive method for measurement of change in intracranial pressure in a patient according to claim 40, wherein the measuring device comprises an ultrasonic pulsed echo system.

42. An apparatus for measuring a change in intercranial pressure in the head of a patient, the patient's head having layers comprised of skin, subcutaneous tissue, bone and intracranial tissue, wherein the interface between the bone and the intracranial tissue is a first interface and the interface between the intracranial tissue and the bone on the opposite side of the patient's head is a second interface, the apparatus comprising:

means for producing and transmitting an electrical tone burst from a reference signal;

means for receiving the electrical tone burst and in response generating a first and second echo in the head of a patient, the first echo reflecting from the first interface in the patient's head and the second echo reflecting from the second interface in the patient's head;

means for receiving the reflected first and second echoes and generating corresponding first and second echo signals; and means for receiving and comparing the first and second echo signals with the reference signal, whereby changes in the intracranial pressure can be related to changes in the measured phase differences.

* * * * *